United States Patent [19]

Yoshida et al.

[11] 4,334,912
[45] Jun. 15, 1982

[54] UREA DERIVATIVES, AND THEIR PRODUCTION AND USE

[75] Inventors: Ryo Yoshida, Kawanishi; Haruhiko Katoh, Takarazuka; Seizo Sumida, Nishinomiya; Ichiki Takemoto; Junya Takahashi, both of Takarazuka; Katsuzo Kamoshita, Osaka, all of Japan

[73] Assignee: Sumitomo Chemical Company, Limited, Osaka, Japan

[21] Appl. No.: 129,980

[22] Filed: Mar. 12, 1980

[30] Foreign Application Priority Data

Mar. 13, 1979 [JP] Japan .................. 54-29549
Aug. 31, 1979 [JP] Japan ................. 54-112313

[51] Int. Cl.³ .............. A01N 43/40; C07D 213/62; C07D 213/64
[52] U.S. Cl. ........................... 71/94; 546/297
[58] Field of Search ................ 71/94; 546/297

[56] References Cited

U.S. PATENT DOCUMENTS 4,003,733 1/1977 Johnston .................. 71/94
4,105,435 8/1978 Nishiyama et al. ........ 71/94
4,123,256 10/1978 Yoshida et al. ........... 71/105
4,129,436 12/1978 Takemoto et al. ......... 71/120

FOREIGN PATENT DOCUMENTS 868406 of 0000 Belgium .

*Primary Examiner*—Catherine L. Mills
*Attorney, Agent, or Firm*—Birch, Stewart, Kolasch & Birch

[57] ABSTRACT

A compound of the formula:

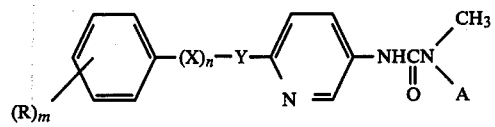

wherein A is a hydrogen atom, a methyl group or a methoxy group, X is a straight or branched $C_1$-$C_4$ alkylene chain, Y is an oxygen atom or a sulfur atom, R, which may be the same or different, is a lower alkyl group, a lower alkoxy group, a trifluoromethyl group, a chlorine atom, a bromine atom or a fluorine atom, m is an integer of 0 to 5 and n is an integer of 0 or 1, provided that in case of R being a fluorine atom, m is an integer of 0 to 5 and in case of R being other than a fluorine atom, m is an integer of 0 to 3, which shows a pronounced herbicidal activity against a wide variety of weeds in the cultivation of crop plants without any material toxicity to mammals and any chemical injury to said crop plants.

14 Claims, No Drawings

UREA DERIVATIVES, AND THEIR PRODUCTION AND USE

The present invention relates to N'-pyridyl-N-methylurea derivatives of the formula:

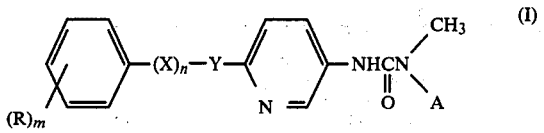

wherein A is a hydrogen atom, a methyl group or a methoxy group, X is a straight or branched $C_1$–$C_4$ alkylene chain, Y is an oxygen atom or a sulfur atom, R, which may be the same or different, is a lower alkyl group, a lower alkoxy group, a trifluoromethyl group, a chlorine atom, a bromine atom or a fluorine atom, m is an integer of 0 to 5 and n is an integer of 0 or 1, provided that in case of R being a fluorine atom, m is an integer of 0 to 5 and in case of R being other than a fluorine atom, m is an integer of 0 to 3, and their production and use.

Rice, wheat, corn, soybean, cotton, sugarbeet and the like are crops of world-wide importance and, in the cultivation of these crops, chemical control of weeds by application of a herbicide is necessary to prevent reduction in the yield. Nevertheless, it has been a recent demand that the herbicide have such a selectivity as to be highly effective on extermination of weeds and yet exert no phytotoxicity on said crop plants.

In order to meet said demand, an extensive study has been made, particularly on substituted urea derivatives, because their herbicidal activity is based on their inhibitory action on photosynthesis, which is a physiological function inherent to higher plants and which does not take place in mammals, and therefore may not produce any harmful effect on mammals. In fact, herbicidal photosynthesis ihibitors such as N'-4-chlorophenyl-N,N-dimethylurea (monuron) and N'-3,4-dichlorophenyl-N,N-dimethylurea (diuron) are all low in mammalian toxicity.

As a result, it was previously found that N'-4-aralkyloxyphenyl-N-methylurea derivatives are effective as herbicides [cf. U.S. Pat. No. 4,123,256; U.S. Pat. No. 4,129,463; Belgian Pat. No. 868,406]. The subsequent study has now revealed that the corresponding pyridyl derivatives as represented by the formula (I) also show a strong herbicidal activity against numerous weeds and, in addition, have various superior properties to the said phenyl derivatives. For instance, N'-[2-(3-trifluoromethylphenyloxy)pyridyl-5]-N-methoxy-N-methylurea (Compound NO. 9) has a higher herbicidal activity on soil treatment with a higher selectivity to wheat than N'-4-(3-trifluoromethylphenyloxy)phenyl-N-methoxy-N-methylurea (Control (a)). Further, for instance, N'-(2-phenethyloxypyridyl-5)-N-methoxy-N-methylurea (Compound No. 13), N'-[2-(4-fluorophenethyloxy)pyridyl-5]-N,N-dimethylurea (Compound No. 34), N'-[2-(3-phenylpropoxy)pyridyl-5]-N,N-dimethylurea (Compound No. 38) and N'-[2-(3-trifluoromethylphenyloxy)pyridyl-5]-N,N-dimethylurea (Compound No. 8) have a higher herbicidal activity on soil treatment with a lower phytotoxicity on wheat than N'-(4-phenethyloxyphenyl)-N-methoxy-N-methylurea (Control (b)), N'-4-(4-fluorophenethyloxy)phenyl-N,N-dimethylurea (Control (c)), N'-4-(3-phenylpropoxy)phenyl-N,N-dimethylurea (Control (d)) and N'-4-(3-trifluoromethylphenoxy)phenyl-N,N-dimethylurea (Control (e)), respectively. Further, for instance, N'-[2-(pentafluorophenoxy)pyridyl-5]-N,N-dimethylurea (Compound No. 51) has a higher herbicidal activity on soil treatment with a lower phytotoxicity on wheat, corn, soybean and cotton than N'-4-(3-trifluoromethylphenoxy)phenyl-N,N-dimethylurea (Control (e)). Furthermore, for instance, N'-(2-phenethyloxypyridyl-5)-N-methoxy-N-methylurea (Compound No. 13) and N'-[2-(4-fluorophenethyloxy)pyridyl-5]-N,N-dimethylurea (Compound No. 34) can exterminate weeds including blackgrass (*Alopecurus geniculatus*), annual bluegrass (*Poa annua*), black nightshade (*Solanum nigrum*), common lambsquarters (*Chenopodium album*), shepherdspurse (*Capsella bursa-pastoris*), bedstraw (*Galium aparine*), chickweed (*Stellaria media*), birdseye speedwell (*Veronica persica*) and red deadnettle (*Lamium purpureum*) on foilage treatment with a reduced phytotoxicity to wheat in comparison with N'-(4-phenethyloxyphenyl)-N-methoxy-N-methylurea (Control (b)) and N'-4-(4-fluorophenethyloxy)phenyl-N,N-dimethylurea (Control (c)).

As understood from the above comparison, the N'-pyridyl-N-methylurea derivatives (I) can exterminate weeds effectively without any material phytotoxicity to wheat not only by soil treatment but also by foilage treatment. Due to their high safety, they can be applied to wheat for a long period of time.

With respect to the N'-pyridyl-N-methylurea derivatives (I), the following two characteristics on the chemical structure may be noted: (1) the presence of a pyridylurea group selected from N'-(pyridyl-3)-N,N-dimethylurea, N'-(pyridyl-3)-N-methoxy-N-methylurea and N'-(pyridyl-3)-N-methylurea, and (2) the existence of a substituent such as substituted phenoxy, substituted phenylthio, substituted phenylalkoxy or substituted phenylalkylthio at the 6-position of the pyridine ring in the pyridylurea group.

Further, the N'-pyridyl-N-methylurea derivatives (I) may be applied not only to wheat fields but also to the fields of corn, rice, soybean, cotton, sugarbeet, etc. by soil treatment or foilage treatment. As shown in Examples 8, 9 and 10 hereinafter presented, for instance, N'-[2-(4-methylphenethyloxy)pyridyl-5]-N-methoxy-N-methylurea (Compound No. 48) is useful as a herbicide for foilage treatment of the fields of wheat and soybean. Further, for instance, N'-[2-(4-isopropoxyphenethyloxy)pyridyl-5]-N-methoxy-N-methylurea (Compound No. 37) may be applied to the fields of soybean and corn without any material phytotoxicity to the crop plants.

Furthermore, as shown in Example 11, the N'-pyridyl-N-methylurea derivatives (I) have a selectivity to rice plants irrespective of the variation on the partial chemical structure.

As stated above, it is clear that the N'-pyridyl-N-methylurea derivatives (I) of the present invention are very effective as selective herbicides for agricultural lands. Also, they are excellent herbicides which can be applied in non-crop lands because of their strong herbicidal activity.

The N'-pyridyl-N-methylurea derivatives (I) are novel and obtainable by reacting an aminopyridine compound of the formula:

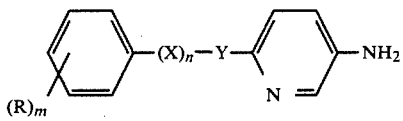

wherein X, Y, R, m and n are each as defined above, with methyl isocyanate, N,N-dimethylcarbamyl chloride or N-methoxy-N-methylcarbamyl chloride. The reaction may be carried out in an inert solvent (e.g. benzene, toluene, xylene, methylene chloride, chloroform, tetrahydrofuran, ethyl acetate, dimethylformamide) at a temperature of 0° to 150° C. for a period of 30 minutes to 10 hours. A base such as pyridine and triethylamine may be advantageously used as an acid-eliminating agent so that the objective compound (I) will be obtained in a better yield. The produced objective compound (I) can be separated from the reaction mixture in a per se conventional manner.

The aminopyridine compound (V), which is the starting material in the above process, is obtainable by reduction of the corresponding nitropyridine compound of the formula:

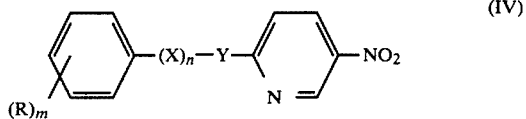

wherein X, Y, R, m and n are each as defined above. The reduction may be accomplished by any conventional procedure such as catalytic reduction using platinum oxide. The reduction may be effected by treatment with hydrogen in the presence of a catalyst such as platinum oxide or palladium in an inert solvent such as ethanol or ethyl acetate under atmospheric or elevated pressure at a temperature of 0° to 60° C. The produced compound (V) may be separated from the reaction mixture by a per se conventional manner.

The nitropyridine compound (IV) is obtainable by condensation between an alcohol or thiol of the formula:

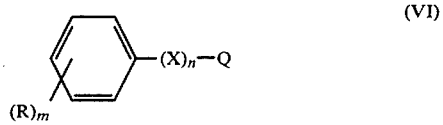

wherein X, R, m and n are each as defined above and Q is a hydroxyl group or a mercapto group, and 2-chloro-5-nitropyridine in the presence or absence of an organic solvent (e.g. benzene, toluene, xylene, tetrahydrofuran, dimethylsulfoxide, dimethylformamide) or water, or a mixture thereof. The presence of a base (e.g. sodium hydroxide, potassium hydroxide, sodium hydride) is advantageous in producing the objective compound in a high yield. A phase transfer catalyst such as a quaternary ammonium salt (e.g. tetra-n-butylammonium bromide) may be also present in the reaction system. The reaction is carried out at a temperature of 10° to 100° C. for a period of 30 minutes to 10 hours. The reaction product may be separated from the reaction mixture by a per se conventional manner.

Some examples of the nitropyridine compound (IV) are shown below:

| Compound No. | Chemical structure | Physical property |
|---|---|---|
| 1a | 3-F₃C-C₆H₄-O-Py-NO₂ | M.P., 35–36° C. |
| 2a | C₆H₅-O-Py-NO₂ | M.P., 86.5–87° C. |
| 3a | C₆H₅-CH₂O-Py-NO₂ | M.P., 101.5–102° C. |
| 4a | 3-H₃C-C₆H₄-CH₂CH₂O-Py-NO₂ | M.P., 73.5–74.5° C. |
| 5a | 2-CH₃O-C₆H₄-CH₂CH₂O-Py-NO₂ | M.P., 47.5–48° C. |
| 6a | C₆H₅-CH₂CH₂O-Py-NO₂ | M.P., 67.5–68° C. |
| 7a | 4-F-C₆H₄-CH₂CH₂O-Py-NO₂ | M.P., 50.5–51° C. |
| 8a | 4-Cl-C₆H₄-CH₂CH₂O-Py-NO₂ | M.P., 89.5–90° C. |
| 9a | C₆H₅-CH₂CH₂CH₂O-Py-NO₂ | M.P., 35.5–36° C. |
| 10a | 4-Br-C₆H₄-CH₂CH₂O-Py-NO₂ | M.P., 117–117.5° C. |
| 11a | 2,6-Cl₂-4-CH₃-C₆H₂-O-Py-NO₂ | M.P., 79–79.5° C. |
| 12a | 4-H₃C-C₆H₄-CH₂CH₂S-Py-NO₂ | M.P., 78.5–79° C. |

Some specific examples of the aminopyridine compound (V) are shown below:

| Compound No. | Chemical structure | Physical property |
|---|---|---|
| 1b | C6H5-O-(pyridyl)-NH2 | M.P., 68–69° C. |
| 2b | Cl-C6H4-O-(pyridyl)-NH2 | M.P., 87–88° C. |
| 3b | C6H5-CH2O-(pyridyl)-NH2 | M.P., 38–39° C. |
| 4b | (t)C4H9-C6H4-CH2CH2O-(pyridyl)-NH2 | B.P., 156–158° C. /0.15 mmHg |
| 5b | (i)C3H7O-C6H4-CH2CH2O-(pyridyl)-NH2 | B.P., 159–162° C. /0.07 mmHg |
| 6b | Br-C6H4-CH2CH2O-(pyridyl)-NH2 | M.P., 49.5–50° C. |
| 7b | H3C,Cl,Cl-C6H2-O-(pyridyl)-NH2 | M.P., 72.5–73° C. |
| 8b | H3C-C6H4-CH2CH2S-(pyridyl)-NH2 | B.P., 157–161° C. /0.15 mmHg |
| 9b | C6H5-CH2CH2CH(CH3)O-(pyridyl)-NH2 | B.P., 159–162° C. /0.1 mmHg |

Some specific examples of the N'-pyridyl-N-methylurea derivative (I) will be shown below but without any intention to limit the scope of the invention thereto:

| Compound No. | Chemical structure | Physical property |
|---|---|---|
| 1 | C6H5-O-(pyridyl)-NH-C(O)-N(CH3)2 | M.P., 132–133° C. |
| 2 | C6H5-O-(pyridyl)-NH-C(O)-N(CH3)(OCH3) | M.P., 102.5–103° C. |
| 3 | Cl-C6H4-O-(pyridyl)-NH-C(O)-N(CH3)2 | M.P., 154–154.5° C. |
| 4 | Cl-C6H4-O-(pyridyl)-NH-C(O)-N(CH3)(OCH3) | M.P., 109–110° C. |
| 5 | H3C,Cl,Cl-C6H2-O-(pyridyl)-NH-C(O)-N(CH3)2 | M.P., 134.5–135° C. |
| 6 | H3C,Cl,Cl-C6H2-O-(pyridyl)-NH-C(O)-N(CH3)(OCH3) | M.P., 152.5–153° C. |

-continued

| Compound No. | Chemical structure | Physical property |
|---|---|---|
| 7 | 4-chloro-2,5-dichloro... 5-methyl-2-[(6-pyridinyl)oxy]-N-methylurea (H₃C, Cl, Cl substituents on phenoxy-pyridine-NH-C(O)-N(CH₃)(H)) | M.P., 163.5–164° C. |
| 8 | 3-(trifluoromethyl)phenoxy-pyridine-NH-C(O)-N(CH₃)₂ | M.P., 116.5–117° C. |
| 9 | 3-(trifluoromethyl)phenoxy-pyridine-NH-C(O)-N(CH₃)(OCH₃) | M.P., 101.5–102° C. |
| 10 | phenyl-CH₂O-pyridine-NH-C(O)-N(CH₃)₂ | M.P., 155–155.5° C. |
| 11 | phenyl-CH₂O-pyridine-NH-C(O)-N(CH₃)(OCH₃) | M.P., 134–135° C. |
| 12 | phenyl-CH₂CH₂O-pyridine-NH-C(O)-N(CH₃)₂ | M.P., 149.5–150° C. |
| 13 | phenyl-CH₂CH₂O-pyridine-NH-C(O)-N(CH₃)(OCH₃) | M.P., 69.5–70° C. |
| 14 | 3-methylphenyl-CH₂CH₂O-pyridine-NH-C(O)-N(CH₃)₂ | M.P., 128.5–129° C. |
| 15 | 3-methylphenyl-CH₂CH₂O-pyridine-NH-C(O)-N(CH₃)(OCH₃) | M.P., 92.5–93° C. |
| 16 | 2-methylphenyl-CH₂CH₂O-pyridine-NH-C(O)-N(CH₃)₂ | M.P., 149.5–150° C. |
| 17 | 2-methylphenyl-CH₂CH₂O-pyridine-NH-C(O)-N(CH₃)(OCH₃) | M.P., 84–85° C. |
| 18 | 4-ethylphenyl-CH₂CH₂O-pyridine-NH-C(O)-N(CH₃)₂ | M.P., 126.5–127° C. |

-continued

| Compound No. | Chemical structure | Physical property |
|---|---|---|
| 19 | $C_2H_5$-C6H4-CH2CH2O-pyridine-NH-C(=O)-N(CH3)(OCH3) | $n_D^{22.0}$ 1.5618 |
| 20 | (t)$C_4H_9$-C6H4-CH2CH2O-pyridine-NH-C(=O)-N(CH3)2 | M.P., 122.5–123° C. |
| 21 | (t)$C_4H_9$-C6H4-CH2CH2O-pyridine-NH-C(=O)-N(CH3)(OCH3) | M.P., 79.5–80° C. |
| 22 | 2,4-(CH3)2-C6H3-CH2CH2O-pyridine-NH-C(=O)-N(CH3)2 | M.P., 140–140.5° C. |
| 23 | 2,4-(CH3)2-C6H3-CH2CH2O-pyridine-NH-C(=O)-N(CH3)(OCH3) | M.P., 90–90.5° C. |
| 24 | 4-CH3O-C6H4-CH2CH2O-pyridine-NH-C(=O)-N(CH3)2 | M.P., 116–116.5° C. |
| 25 | 4-CH3O-C6H4-CH2CH2O-pyridine-NH-C(=O)-N(CH3)(OCH3) | M.P., 85–85.5° C. |
| 26 | 3-CH3O-C6H4-CH2CH2O-pyridine-NH-C(=O)-N(CH3)2 | M.P., 110–110.5° C. |
| 27 | 3-CH3O-C6H4-CH2CH2O-pyridine-NH-C(=O)-N(CH3)(OCH3) | M.P., 65–65.5° C. |
| 28 | 2-CH3O-C6H4-CH2CH2O-pyridine-NH-C(=O)-N(CH3)2 | M.P., 120–120.5° C. |
| 29 | 2-CH3O-C6H4-CH2CH2O-pyridine-NH-C(=O)-N(CH3)(OCH3) | M.P., 86.5–87° C. |
| 30 | 4-Cl-C6H4-CH2CH2O-pyridine-NH-C(=O)-N(CH3)2 | M.P., 169.5–170° C. |
| 31 | 4-Cl-C6H4-CH2CH2O-pyridine-NH-C(=O)-N(CH3)(OCH3) | M.P., 86.5–87° C. |

-continued

| Compound No. | Chemical structure | Physical property |
|---|---|---|
| 32 | Br-C6H4-CH2CH2O-[pyridine]-NH-C(=O)-N(CH3)2 | M.P., 153.5–154° C. |
| 33 | Br-C6H4-CH2CH2O-[pyridine]-NH-C(=O)-N(CH3)(OCH3) | M.P., 79.5–80° C. |
| 34 | F-C6H4-CH2CH2O-[pyridine]-NH-C(=O)-N(CH3)2 | M.P., 68.5–69° C. |
| 35 | F-C6H4-CH2CH2O-[pyridine]-NH-C(=O)-N(CH3)(OCH3) | M.P., 56.5–57° C. |
| 36 | (i)C3H7O-C6H4-CH2CH2O-[pyridine]-NH-C(=O)-N(CH3)2 | M.P., 125.5–126° C. |
| 37 | (i)C3H7-C6H4-CH2CH2O-[pyridine]-NH-C(=O)-N(CH3)(OCH3) | M.P., 60–61° C. |
| 38 | C6H5-CH2CH2O-[pyridine]-NH-C(=O)-N(CH3)2 | M.P., 145–145.5° C. |
| 39 | C6H5-CH2CH2O-[pyridine]-NH-C(=O)-N(CH3)(OCH3) | M.P., 93.5–94° C. |
| 40 | C6H5-CH2CH2CH2O-[pyridine]-NH-C(=O)-N(CH3)2 | M.P., 121.5–122° C. |
| 41 | C6H5-CH2CH2CH2O-[pyridine]-NH-C(=O)-N(CH3)(OCH3) | M.P., 95.5–96° C. |
| 42 | H3C-C6H4-CH2CH2S-[pyridine]-NH-C(=O)-N(CH3)2 | M.P., 115.5–116° C. |
| 43 | H3C-C6H4-CH2CH2S-[pyridine]-NH-C(=O)-N(CH3)(OCH3) | M.P., 84.5–85° C. |
| 44 | C6H5-CH2CH2CH(CH3)O-[pyridine]-NH-C(=O)-N(CH3)2 | M.P., 129–129.5° C. |
| 45 | C6H5-CH2CH2CH(CH3)O-[pyridine]-NH-C(=O)-N(CH3)(OCH3) | $n_D^{22.0}$ 1.5578 |
| 46 | H3C-C6H4-CH2CH2O-[pyridine]-NH-C(=O)-N(CH3)2 | M.P., 85–86° C. |

-continued

| Compound No. | Chemical structure | Physical property |
|---|---|---|
| 47 | CH₃O–⟨C₆H₄⟩–CH₂CH₂O–⟨pyridine⟩–NH–C(=O)–N(CH₃)(H) | M.P., 145–145.5° C. |
| 48 | H₃C–⟨C₆H₄⟩–CH₂CH₂O–⟨pyridine⟩–NH–C(=O)–N(CH₃)(OCH₃) | M.P., 85–86° C. |
| 49 | 2-Cl-⟨C₆H₄⟩–CH₂CH₂O–⟨pyridine⟩–NH–C(=O)–N(CH₃)₂ | M.P., 132–133° C. |
| 50 | 2-Cl-⟨C₆H₄⟩–CH₂CH₂O–⟨pyridine⟩–NH–C(=O)–N(CH₃)(OCH₃) | M.P., 77.5–78° C. |
| 51 | C₆F₅–O–⟨pyridine⟩–NH–C(=O)–N(CH₃)₂ | M.P., 186–187° C. |
| 52 | C₆F₅–O–⟨pyridine⟩–NH–C(=O)–N(CH₃)(OCH₃) | M.P., 131–131.5° C. |
| 53 | 4-F-⟨C₆H₄⟩–O–⟨pyridine⟩–NH–C(=O)–N(CH₃)₂ | M.P., 157–157.5° C. |
| 54 | 4-F-⟨C₆H₄⟩–O–⟨pyridine⟩–NH–C(=O)–N(CH₃)(OCH₃) | M.P., 104.5–105° C. |
| 55 | 3-Cl-⟨C₆H₄⟩–O–⟨pyridine⟩–NH–C(=O)–N(CH₃)₂ | M.P., 145–145.5° C. |
| 56 | 3-F-⟨C₆H₄⟩–CH₂O–⟨pyridine⟩–NH–C(=O)–N(CH₃)₂ | M.P., 124.5–125° C. |
| 57 | 3-F-⟨C₆H₄⟩–CH₂O–⟨pyridine⟩–NH–C(=O)–N(CH₃)(OCH₃) | M.P., 83.5–84° C. |
| 58 | 4-H₃C-⟨C₆H₄⟩–O–⟨pyridine⟩–NH–C(=O)–N(CH₃)₂ | M.P., 151.5–152° C. |

-continued

| Compound No. | Chemical structure | Physical property |
|---|---|---|
| 59 | H₃C–⟨phenyl⟩–O–⟨pyridyl(N)⟩–NH–C(=O)–N(CH₃)(OCH₃) | M.P., 108.5–109° C. |
| 60 | 2,4-Cl₂–⟨phenyl⟩–O–⟨pyridyl(N)⟩–NH–C(=O)–N(CH₃)(CH₃) | M.P., 155.5–156° C. |
| 61 | 2,4-Cl₂–⟨phenyl⟩–O–⟨pyridyl(N)⟩–NH–C(=O)–N(CH₃)(OCH₃) | M.P., 115.5–116° C. |
| 62 | H₃C–⟨phenyl⟩–CH₂CH₂CH₂O–⟨pyridyl(N)⟩–NH–C(=O)–N(CH₃)(CH₃) | M.P., 141–142° C. |
| 63 | H₃C–⟨phenyl⟩–CH₂CH₂CH₂O–⟨pyridyl(N)⟩–NH–C(=O)–N(CH₃)(OCH₃) | $n_D^{22.0}$ 1.5250 |
| 64 | F–⟨phenyl⟩–CH₂CH₂CH₂O–⟨pyridyl(N)⟩–NH–C(=O)–N(CH₃)(OCH₃) | M.P., 63–64° C. |
| 65 | H₃C–⟨phenyl⟩–CH₂CH₂CH₂CH₂O–⟨pyridyl(N)⟩–NH–C(=O)–N(CH₃)(CH₃) | M.P., 120.5–121° C. |
| 66 | H₃C–⟨phenyl⟩–CH₂CH₂CH₂CH₂O–⟨pyridyl(N)⟩–NH–C(=O)–N(CH₃)(OCH₃) | M.P., 84.5–85° C. |
| 67 | F₃C–⟨phenyl⟩–O–⟨pyridyl(N)⟩–NH–C(=O)–N(CH₃)(CH₃) | M.P., 167–167.5° C. |
| 68 | F₃C–⟨phenyl⟩–O–⟨pyridyl(N)⟩–NH–C(=O)–N(CH₃)(OCH₃) | M.P., 80.5–81° C. |

Some practical examples of the process for preparing the N'-pyridyl-N-methylurea derivatives (I) are illustratively shown below.

EXAMPLE 1

Synthesis of 2-(3-methylphenethyloxy)-5-nitropyridine

To a solution of 4.8 g of sodium hydride (50% oily suspension) in 130 ml of dimethylformamide, was added dropwise 13.6 g of 3-methylphenethyl alcohol in 20 minutes, and the resultant mixture was heated at 60° C. for 2 hours. After cooling, a solution of 15.9 g of 2-chloro-5-nitropyridine in 80 ml of dimethylformamide was added dropwise thereto at a temperature below 20° C. under ice-cooling. After standing at room temperature overnight, the reaction mixture was poured into ice water, followed by extraction with ethyl acetate. The extracts were washed with water and dried over magnesium sulfate. The oily products were purified by column chromatography on silica gel using benzene as an eluent to give 20.4 g of 2-(3-methylphenethyloxy)-5-nitropyridine as white crystals. M.P., 73.5°–74.5° C.

Elementary analysis: Calcd. for $C_{14}H_{14}N_2O_3$: C, 65.10%; H, 5.46%; N, 10.85%. Found: C, 65.13%; H, 5.41%; N, 11.01%.

NMR$\delta_{CDCl_3}$: 2.32 (s, 3H), 3.02 (t, 2H), 4.61 (t, 2H), 6.70 (d, 1H), 7.05 (s, 4H), 8.26 (q, 1H), 9.00 (d, 1H).

EXAMPLE 2

Synthesis of 4-chlorophenoxy-5-aminopyridine

4-Chlorophenoxy-5-nitropyridine (19.9 g) and platinum dioxide (0.1 g) were suspended in a mixture of tetrahydrofuran (100 ml) and ethyl acetate (50 ml), and catalytic reduction was carried out until 5.0 liters of hydrogen were absorbed. After removal of the catalyst by filtration, the solvent was distilled out under reduced pressure. The precipitated crystals were washed with a small amount of ether to give 16.5 g of 4-chlorophenoxy-5-aminopyridine as white crystals. M.P., 87°–88° C.

Elementary analysis: Calcd. for $C_{11}H_9N_2OCl$: C, 59.81%; H, 4.11%; Cl, 16.05%; N, 12.69%. Found: C, 59.98%; H, 4.02%; Cl, 15.99%; N, 12.49%.

NMR$\delta_{CDCl_3}$: 3.51 (s, 2H), 6.70 (d, 1H), 6.85–7.65 (6H).

EXAMPLE 3

Synthesis of N′-[2-(3-trifluoromethylphenoxy)pyridyl-5]-N-methoxy-N-methylurea

To a solution of 2-(3-trifluoromethylphenoxy)-5-aminopyridine (8 g) in 50 ml of pyridine was added dropwise a solution of 4 g of N-methoxy-N-methylcarbamyl chloride in 10 ml of benzene under ice-cooling. After standing at room temperature for 3 hours, the resultant mixture was poured into ice water, followed by extraction with ethyl acetate. The extracts were washed with water and dried over magnesium sulfate. Thereafter, the solvent was removed under reduced pressure, and the precipitated crystals were recrystallized from ethanol to give 9 g of N′-[2-(3-trifluoromethylphenoxy)pyridyl-5]-N-methoxy-N-methylurea as white crystals. M.P., 101.5°–102° C.

Elementary analysis: Calcd. for $C_{15}H_{14}O_3N_3F_3$: C, 52.68%; H, 4.13%; N, 12.29%; F, 16.67%. Found: C, 52.72%; H, 4.09%; N, 12.38%; F, 16.50%.

NMR$\delta_{CDCl_3}$: 3.19 (s, 3H), 3.75 (s, 3H), 6.95 (d, 1H), 7.25–8.20 (7H).

EXAMPLE 4

Synthesis of N′-[2-(4-fluorophenethyloxy)pyridyl-5]-N,N-dimethylurea

To a solution of 2-(4-fluorophenethyloxy)-5-aminopyridine (2.0 g) in 10 ml of pyridine was added dropwise a solution of 1.0 g of N,N-dimethylcarbamyl chloride in 1 ml of benzene under ice-cooling. After standing at room temperature for 12 hours, the resultant mixture was poured into ice water, followed by extraction with ethyl acetate. The extracts were washed with water and dried over magnesium sulfate. Thereafter, the solvent was removed by distillation under reduced pressure, and the precipitated crystals were recrystallized from ethanol to give 2.4 g of N′-[2-(4-fluorophenethyloxy)pyridyl-5]-N,N-dimethylurea as white crystals. Yield, 87%. M.P., 68.5°–69° C.

Elementary analysis: Calcd. for $C_{16}H_{18}O_2N_3F$: C, 63.24%; H, 5.97%; N, 13.83%; F, 6.25%. Found: C, 63.31%; H, 5.87%; N, 13.70%; F, 6.18%.

NMR$\delta_{CDCl_3}$: 2.97 (s, 6H), 3.01 (2H), 4.45 (t, 2H), 6.34 (s, 1H), 6.65 (d, 1H), 6.76–7.42 (4H), 7.74 (q, 1H), 7.98 (d, 1H).

EXAMPLE 5

Synthesis of 2-(4-methylphenethyloxy)-5-nitropyridine

To a solution of sodium hydride (60% oily suspension) (8.0 g) in 200 ml of dimethylsulfoxide was added dropwise 27.2 g of p-methylphenethyl alcohol at a temperature below 20° C. under ice-cooling, followed by stirring at room temperature for 1 hour. To the resultant mixture, was added dropwise a solution of 31.7 g of 2-chloro-5-nitropyridine in 100 ml of dimethylsulfoxide, and the resulting mixture was heated at 60° C. for 1 hour. After cooling, the reaction mixture was poured into ice water and extracted with ethyl acetate. The extracts were washed with water and dried over magnesium sulfate. After removal of the solvent, the oily products were purified by column chromatography on silica gel using benzene as an eluent to give 28.9 g of 2-(4-methylphenethyloxy)-5-nitropyridine as yellow crystals. Yield, 56%. M.P., 85°–85.5° C.

Elementary analysis: Calcd. for $C_{14}H_{14}N_2O_3$: C, 65.10%; H, 5.46%; N, 10.85%. Found: C, 65.04%; H, 5.65%; N, 10.71%.

NMR$\delta_{CDCl_3}$: 2.33 (s, 3H), 3.10 (t, 2H), 4.66 (t, 2H), 6.83 (d, 1H), 7.18 (s, 4H), 8.33 (q, 1H), 9.08 (q, 1H).

EXAMPLE 6

Synthesis of 2-(4-methylphenethyloxy)-5-aminopyridine 2-(4-Methylphenethyloxy)-5-nitropyridine (3.7 g) and 1.7 g of 5% palladium charcoal were suspended in 37 ml of ethanol, and catalytic reduction was carried out until 1.1 liters of hydrogen were absorbed. After removal of the catalyst by filtration, the solvent was distilled out under reduced pressure. The crystals were collected on a glass filter and washed with ether to give 3.1 g of 2-(4-methylphenethyloxy)-5-aminopyridine as yellow crystals. Yield, 84.9%. M.P., 64.5°–65° C.

Elementary analysis: Calcd. for $C_{14}H_{16}N_2O$: C, 73.65%; H, 7.06%; N, 12.27%. Found: C, 73.47%; H, 7.01%; N, 12.36%.

NMR$\delta_{CDCl_3}$: 2.29 (s, 3H), 2.99 (t, 2H), 3.30 (s, 2H), 4.38 (t, 2H), 6.50 (d, 1H), 6.92 (q, 1H), 7.09 (s, 4H), 7.56 (d, 1H).

EXAMPLE 7

Synthesis of N′-[2-(4-methylphenethyloxy)pyridyl-5]-N-methoxy-N-methylurea

To a solution of 2-(4-methylphenethyloxy)-5-aminopyridine (0.6 g) in 2 ml of pyridine was added dropwise a solution of 0.64 g of N-methoxy-N-methylcarbamyl chloride in 3 ml of benzene under ice-cooling. After standing at room temperature for 3 hours, the resultant mixture was poured into ice water, and extracted with ethyl acetate. The extracts were washed with water and dried over magnesium sulfate. After removal of the solvent under reduced pressure, the crystals were collected on a glass filter and washed with ether to give 0.5 g of N′-[2-(4-methylphenethyloxy)-pyridyl-5]-N-methoxy-N-methylurea as white crystals. Yield, 64.2%. M.P., 85°–86° C.

Elementary analysis: Calcd. for $C_{17}H_{21}N_3O_3$: C, 64.74%; H, 6.71%; N, 13.33%. Found: C, 64.68%; H, 6.60%; N, 13.51%.

NMR$\delta_{CDCl_3}$: 2.31 (s, 3H), 3.02 (t, 2H), 3.15 (s, 3H), 3.72 (s, 3H), 4.46 (t, 2H), 6.67 (d, 1H), 7.11 (s, 4H), 7.52 (s, 1H), 7.80 (q, 1H), 8.06 (d, 1H).

In the practical use of the N′-pyridyl-N-methylurea derivatives (I), they may be applied as such or in any preparation form such as wettable powders, emulsifiable concentrates, granules, fine granules or dusts.

In producing such preparation form, a solid or liquid carrier may be used. As for the solid carrier, there may be mentioned mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like.

As for the liquid carrier, there may be mentioned alcohols (e.g. methyl alcohol, ethyl alcohol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methyl ethyl ketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene-oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfate, quaternary ammonium salts, oxyalkylamine and the like. But, the surface active agent is not of course limited to these compounds. And, if necessary, gelatin, casein, sodium alginate, starch, agar, polyvinyl alcohol or the like may be used as an auxiliary agent.

In the preparation of a herbicidal composition, the content of the compound (I) may be from 1 to 95% by weight, preferably from 1 to 80% by weight.

Practical embodiments of the herbicidal composition according to the invention are illustratively shown in the following examples wherein parts and % are by weight.

PREPARATION EXAMPLE 1

Eighty parts of Compound No. 9, 5 parts of polyoxyethylene alkylaryl ether and 15 parts of synthetic silicon oxide hydrate are well mixed while being powdered to obtain a wettable powder.

PREPARATION EXAMPLE 2

Thirty parts of Compound No. 31, 7 parts of polyoxyethylene alkylaryl ether, 3 parts of alkylaryl sulfonate and 60 parts of xylene are well mixed to obtain an emulsifiable concentrate.

PREPARATION EXAMPLE 3

One part of Compound No. 33, 1 part of white carbon, 5 parts of ligninsulfonate and 93 parts of clay are well mixed while being powdered. The mixture is then well kneaded with water, granulated and dried to obtain a granule.

PREPARATION EXAMPLE 4

Forty parts of bentonite, 5 parts of lignin-sulfonate and 55 parts of clay are well mixed while being powdered. The mixture is then well kneaded with water, granulated and dried to obtain a granule containing no active ingredient. The granule is then impregnated with 5 parts of Compound No. 35 to obtain a granule.

PREPARATION EXAMPLE 5

Three parts of Compound No. 8, 0.5 parts of isopropyl phosphate, 66.5 parts of clay and 30 parts of talc are well mixed while being powdered to obtain a dust.

PREPARATION EXAMPLE 6

Eighty parts of Compound No. 48, 5 parts of polyoxyethylene alkylaryl ether and 15 parts of synthetic silicon oxide hydrate are well mixed while being powdered to obtain a wettable powder.

PREPARATION EXAMPLE 7

Thirty parts of Compound No. 48, 7 parts of polyoxyethylene alkylaryl ether, 3 parts of alkylaryl sulfonate and 60 parts of xylene are well mixed to obtain an emulsifiable concentrate.

PREPARATION EXAMPLE 8

One part of Compound No. 48, 1 part of white carbon, 5 parts of ligninsulfonate and 93 parts of clay are well mixed while being powdered. The mixture is then well kneaded with water, granulated and dried to obtain a granule.

PREPARATION EXAMPLE 9

Forty parts of bentonite, 5 parts of lignin-sulfonate and 55 parts of clay are well mixed while being powdered. The mixture is then well kneaded with water, granulated and dried to obtain a granule containing no active ingredient. The granule is then impregnated with 5 parts of Compound No. 48 to obtain a granule.

PREPARATION EXAMPLE 10

Three parts of Compound No. 48, 0.5 parts of isopropyl phosphate, 66.5 parts of clay and 30 parts of talc are well mixed while being powdered to obtain a dust.

The N'-pyridyl-N-methylurea derivatives (I) of the invention may be used together with other herbicides to improve their activity as herbicides, and in some cases, a synergistic effect can be expected. As the other herbicides, there may be given phenoxy series herbicides such as 2,4-dichlorophenoxyacetic acid and 2,4-dichlorophenoxybutyric acid (including esters and salts thereof); diphenyl ether series herbicides such as 2,4-dichlorophenyl-4'-nitrophenyl ether, 2,4-dichlorophenyl-4'-nitro-3'-methoxyphenyl ether, 2,4-dichlorophenyl-3'-methoxycarbonyl-4'-nitrophenyl ether and 2-chloro-4-trifluoromethylphenyl-3'-hydroxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine and 2-methylthio-4,6-bisethylamino-1,3,5-triazine; urea series herbicides such as 3-(3,4-dichlorophenyl)-1,1-dimethylurea, 3-(3,4-dichlorophenyl)-1-methoxy-1-methylurea, 3-[4-(4-chlorophenoxy)phenyl]-1,1-dimethylurea and 3-[$\alpha,\alpha,\alpha$-trifluoro-m-tolyl)-1,1-dimethylurea; carbamate series herbicides such as isopropyl-N-(3-chlorophenyl)carbamate, methyl-N-(3,4-dichlorophenyl)carbamate and 4-chloro-2-butynyl-m-chlorocarbanilate; thiolcarbamate series herbicides such as S-(4-chlorobenzyl)-N,N-diethylthiolcarbamate and S-ethyl dipropylthiolcarbamate; acid anilide series herbicides such as 3,4-dichloropropionanilide, N-methoxymethyl-2,6-diethyl-2-chloroacetanilide and 2-chloro-2',6'-diethyl-N-(butoxymethyl)acetanilide; uracil series herbicides such as 5-bromo-3-sec-butyl-6-methyluracil and 3-cyclohexyl-5,6-trimethyleneuracil; pyridinium salt series herbicides such as 1,1'-dimethyl-4,4'-bispyridinium dichloride; phosphorus series herbicides such as N-(phosphonomethyl)glycine, O-methyl-O-(2-nitro-4-methylphenyl)-N-isopropylphosphoroamidothioate and O-ethyl-O-(2-nitro-5-methylphenyl)-N-sec-butylphosphoroamidothioate; toluidine series herbicides such as α,α,α-trifluoro-2,6-dinitro-N,N-dipropyl-p-toluidine; N-sec-butyl-4-tert-butyl-2,6-dinitroaniline; 3,5-dinitro-N⁴,N⁴-dipropylsulfanylamide; 5-tert-butyl-3-(2,4-dichloro-5-isopropoxyphenyl)-1,3,4-oxadiazolin-2-one; 3-isopropyl-1H-2,1,3-benzothiadiazine(4)-3H-one-2,2-dioxide (including salts thereof); 2-(β-naphthoxy)propionanilide; 2-(α-naphthoxy)-N,N-diethylpropionanilide; 3-amino-2,5-dichlorobenzoic acid; 2-sec-butyl-4,6-dinitrophenyl; N-1-naphthylphthalamic acid and the like. But, the herbicides are not of course limited to these examples.

The herbicides of the invention may be applied together with microbial pesticides, organophosphoric series insecticides, carbamate series insecticides, pyrethroid series insecticides, other insecticides, fungicides, plant growth regulators, fertilizers, etc.

The dosage rate of the compound (I) depends upon their kinds, the sorts of cultivated plants, the method of application, etc. Generally, however, the dosage rate is from 0.5 to 200 grams, preferably from 2 to 80 grams, of the active ingredient per are.

The application of the N'-pyridyl-N-methylurea derivatives (I) as herbicides will be illustrated in the following Examples wherein the phytotoxicity to cultivated plants and the herbicidal activity on weeds were evaluated as follows: the aereal parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5 and 4, are generally regarded as satisfactory to protect cultivated plants and to control weeds, respectively. The rating values in the paddy rice test alone were calculated from the dry weight of the plant.

| Rating value | Fresh weight (percentage to untreated plot) | |
|---|---|---|
| | Cultivated plant | Weed |
| 5 | 0–39 | 0 |
| 4 | 40–59 | 1–10 |
| 3 | 60–79 | 11–20 |
| 2 | 80–89 | 21–40 |
| 1 | 90–99 | 41–60 |
| 0 | 100 | 61–100 |

The following control compounds were used in the Examples.

Chloroxuron

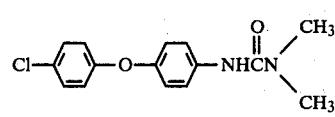

Fluometuron

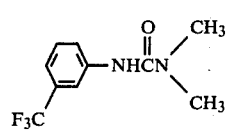

Chloramben

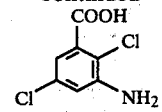

MCPA

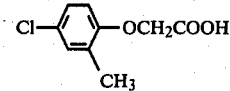

Control (a)

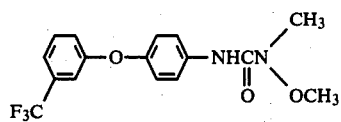

Control (b)

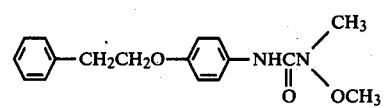

Control (c)

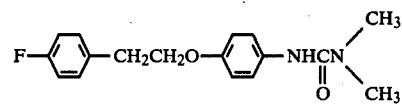

Control (d)

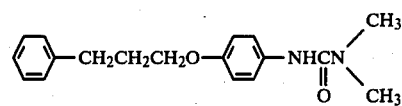

Control (e)

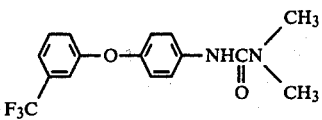

(Belgian Pat. 845,528)

EXAMPLE 8

Post-emergence application

Plastic trays (35 cm×25 cm×10 cm (high) were filled with upland field soil, and the seeds of redroot pigweed (*Amaranthus retroflexus* L.), common lambsquarters (*Chenopodium album*), radish, sunflower, cocklebur (*Xanthium chinense*), annual morningglory (*Ipomoea purpurea*), black nightshade (*Solanum nigrum*), large crabgrass (*Digitaria sanguinalis*), barnyard grass (*Echinochloa crusgalli*) and green foxtail (*Setaria viridis*) were separately sowed in the trays and grown for 2 to 3 weeks in a greenhouse. The required amount of the test compound was sprayed to the foliage of the test plants over the top by means of a small hand sprayer. After the spraying, the test plants were grown for an additional 3 weeks in the greenhouse, and the herbicidal activity was examined. The results are shown in Table 1. In the above foliar application, the test compounds were each formulated into an emulsifiable concentrate, and the required amount of the emulsifiable concentrate was dispersed in water for application at a spray volume of 5 liters per are and applied with the addition of a wetting agent. At the time of application, the weeds were in a 2- to 4-leaf stage and 2 to 10 cm in height.

TABLE 1

| Compound No. | Dosage (weight of active ingredient, g/are) | Redroot pigweed | Common lambs-quarters | Radish | Sunflower | Cocklebur | Annual morning glory | Black nightshade | Large crabgrass | Barnyard grass | Greenfoxtail |
|---|---|---|---|---|---|---|---|---|---|---|---|
| 3 | 20 | 5 | 5 | 5 | 5 | 5 | 5 | 5 | 4 | 4 | 4 |
|  | 10 | 5 | 5 | 5 | 5 | 5 | 5 | 5 | 4 | 3 | 4 |
| 8 | 20 | 5 | 5 | 5 | 5 | 5 | 5 | 5 | 5 | 4 | 5 |
|  | 10 | 5 | 5 | 5 | 5 | 5 | 5 | 5 | 4 | 4 | 4 |
| 9 | 10 | 5 | 5 | 5 | 5 | 5 | 5 | 5 | 5 | 5 | 5 |
|  | 5 | 5 | 5 | 5 | 5 | 5 | 5 | 5 | 4 | 4 | 4 |
| 12 | 20 | 5 | 5 | 5 | 5 | 5 | 5 | 5 | 5 | 4 | 5 |
|  | 10 | 5 | 5 | 5 | 5 | 5 | 5 | 5 | 4 | 4 | 4 |
| 13 | 20 | 5 | 5 | 5 | 5 | 5 | 5 | 5 | 5 | 5 | 5 |
|  | 10 | 5 | 5 | 5 | 5 | 5 | 5 | 5 | 4 | 4 | 5 |
| 15 | 20 | 5 | 5 | 5 | 5 | 5 | 5 | 5 | 4 | 4 | 4 |
|  | 10 | 5 | 5 | 5 | 5 | 5 | 5 | 5 | 3 | 4 | 4 |
| 21 | 20 | 5 | 5 | 5 | 5 | 5 | 5 | 5 | 4 | 5 | 4 |
|  | 10 | 5 | 5 | 5 | 5 | 5 | 5 | 5 | 3 | 3 | 4 |
| 22 | 20 | 5 | 5 | 5 | 5 | 5 | 5 | 5 | 5 | 5 | 5 |
|  | 10 | 5 | 5 | 5 | 5 | 5 | 5 | 5 | 3 | 3 | 4 |
| 23 | 20 | 5 | 5 | 5 | 5 | 5 | 5 | 5 | 4 | 4 | 4 |
|  | 10 | 5 | 5 | 5 | 5 | 5 | 5 | 5 | 3 | 4 | 3 |
| 24 | 40 | 5 | 5 | 5 | 5 | 5 | 5 | 5 | 4 | 4 | 4 |
|  | 20 | 5 | 5 | 5 | 5 | 5 | 5 | 5 | 3 | 4 | 3 |
| 26 | 20 | 5 | 5 | 5 | 5 | 5 | 5 | 5 | 4 | 5 | 4 |
|  | 10 | 5 | 5 | 5 | 5 | 5 | 5 | 5 | 4 | 3 | 4 |
| 27 | 20 | 5 | 5 | 5 | 5 | 5 | 5 | 5 | 4 | 4 | 5 |
|  | 10 | 5 | 5 | 5 | 5 | 5 | 5 | 5 | 3 | 4 | 4 |
| 29 | 40 | 5 | 5 | 5 | 5 | 5 | 5 | 5 | 4 | 4 | 4 |
|  | 20 | 5 | 5 | 5 | 5 | 5 | 5 | 5 | 4 | 3 | 3 |
| 31 | 10 | 5 | 5 | 5 | 5 | 5 | 5 | 5 | 5 | 5 | 5 |
|  | 5 | 5 | 5 | 5 | 5 | 5 | 5 | 5 | 4 | 4 | 5 |
| 33 | 10 | 5 | 5 | 5 | 5 | 5 | 5 | 5 | 5 | 4 | 5 |
|  | 5 | 5 | 5 | 5 | 5 | 5 | 5 | 5 | 4 | 4 | 4 |
| 34 | 20 | 5 | 5 | 5 | 5 | 5 | 5 | 5 | 4 | 3 | 4 |
|  | 10 | 5 | 5 | 5 | 5 | 5 | 5 | 5 | 2 | 3 | 3 |
| 35 | 10 | 5 | 5 | 5 | 5 | 5 | 5 | 5 | 4 | 5 | 5 |
|  | 5 | 5 | 5 | 5 | 5 | 5 | 5 | 5 | 4 | 4 | 4 |
| 36 | 20 | 5 | 5 | 5 | 5 | 5 | 5 | 5 | 4 | 5 | 4 |
|  | 10 | 5 | 5 | 5 | 5 | 5 | 5 | 5 | 3 | 3 | 4 |
| 37 | 20 | 5 | 5 | 5 | 5 | 5 | 5 | 5 | 4 | 4 | 4 |
|  | 10 | 5 | 5 | 5 | 5 | 5 | 5 | 5 | 3 | 4 | 3 |
| 38 | 40 | 5 | 5 | 5 | 5 | 5 | 5 | 5 | 4 | 4 | 5 |
|  | 20 | 5 | 5 | 5 | 5 | 5 | 5 | 5 | 3 | 3 | 3 |
| 39 | 20 | 5 | 5 | 5 | 5 | 5 | 5 | 5 | 5 | 4 | 5 |
|  | 10 | 5 | 5 | 5 | 5 | 5 | 5 | 5 | 3 | 4 | 4 |
| 43 | 40 | 5 | 5 | 5 | 5 | 5 | 5 | 5 | 5 | 4 | 4 |
|  | 20 | 5 | 5 | 5 | 5 | 5 | 5 | 5 | 3 | 4 | 3 |
| 44 | 40 | 5 | 5 | 5 | 5 | 5 | 5 | 5 | 4 | 4 | 4 |
|  | 20 | 5 | 5 | 5 | 5 | 5 | 5 | 5 | 3 | 3 | 4 |
| 46 | 40 | 5 | 5 | 5 | 5 | 5 | 5 | 5 | 4 | 4 | 4 |
|  | 20 | 5 | 5 | 5 | 5 | 5 | 5 | 5 | 3 | 4 | 3 |
| 48 | 20 | 5 | 5 | 5 | 5 | 5 | 5 | 5 | 5 | 4 | 5 |
|  | 10 | 5 | 5 | 5 | 5 | 5 | 5 | 5 | 4 | 3 | 4 |
| 49 | 20 | 5 | 5 | 5 | 5 | 5 | 5 | 5 | 3 | 3 | 4 |
|  | 10 | 5 | 5 | 5 | 4 | 4 | 5 | 5 | 2 | 1 | 2 |
| 50 | 20 | 5 | 5 | 5 | 5 | 5 | 5 | 5 | 5 | 4 | 5 |
|  | 10 | 5 | 5 | 5 | 5 | 5 | 5 | 5 | 3 | 3 | 3 |
| 51 | 20 | 5 | 5 | 5 | 5 | 5 | 5 | 5 | 5 | 5 | 5 |
|  | 10 | 5 | 5 | 5 | 5 | 5 | 5 | 5 | 4 | 3 | 4 |
| 52 | 20 | 5 | 5 | 5 | 5 | 5 | 5 | 5 | 5 | 4 | 5 |
|  | 10 | 5 | 5 | 5 | 5 | 5 | 5 | 5 | 4 | 4 | 3 |
| 56 | 40 | 5 | 5 | 5 | 5 | 5 | 5 | 5 | 3 | 4 | 4 |
|  | 20 | 5 | 5 | 5 | 5 | 4 | 4 | 5 | 2 | 3 | 3 |
| 59 | 20 | 5 | 5 | 5 | 5 | 5 | 5 | 5 | 4 | 4 | 5 |
|  | 10 | 5 | 5 | 5 | 5 | 5 | 5 | 5 | 3 | 3 | 4 |
| 60 | 20 | 5 | 5 | 5 | 5 | 5 | 5 | 5 | 4 | 4 | 4 |
|  | 10 | 5 | 5 | 5 | 5 | 5 | 5 | 5 | 2 | 3 | 3 |
| 61 | 20 | 5 | 5 | 5 | 5 | 5 | 5 | 5 | 4 | 3 | 4 |
|  | 10 | 5 | 5 | 5 | 5 | 5 | 5 | 5 | 3 | 2 | 3 |
| 63 | 20 | 5 | 5 | 5 | 5 | 5 | 5 | 5 | 4 | 4 | 3 |
|  | 10 | 5 | 5 | 5 | 5 | 5 | 5 | 5 | 3 | 2 | 2 |
| 64 | 20 | 5 | 5 | 5 | 5 | 5 | 5 | 5 | 5 | 5 | 5 |
|  | 10 | 5 | 5 | 5 | 5 | 5 | 5 | 5 | 4 | 4 | 5 |
| 66 | 20 | 5 | 5 | 5 | 5 | 5 | 5 | 5 | 4 | 4 | 5 |
|  | 10 | 5 | 5 | 5 | 5 | 5 | 5 | 5 | 3 | 4 | 3 |
| 68 | 20 | 5 | 5 | 5 | 5 | 5 | 5 | 5 | 4 | 4 | 4 |

TABLE 1-continued

| Compound No. | Dosage (weight of active ingredient, g/are) | Herbicidal activity | | | | | | | | |
|---|---|---|---|---|---|---|---|---|---|---|
| | | Redroot pigweed | Common lambs-quarters | Radish | Sun-flower | Cocklebur | Annual morning glory | Black night-shade | Large crab-grass | Barn-yard grass | Green-foxtail |
| | 10 | 5 | 5 | 5 | 5 | 5 | 5 | 5 | 2 | 2 | 3 |
| Fluo-meturon | 20 | 5 | 5 | 5 | 5 | 5 | 5 | 5 | 4 | 3 | 4 |
| | 10 | 5 | 5 | 3 | 4 | 3 | 4 | 3 | 4 | 2 | 3 |

EXAMPLE 9

Selectivity on crop plants by post-emergence application

Wagner's pots (1/5000 are) were each filled with paddy field soil, and the seeds of soybean, cotton, sugarbeet, corn, wheat and rice plants were separately sown in the pots and grown for 2 to 3 weeks in the greenhouse. The required amount of the test compound was sprayed to the foliage of the test plants over the top by means of a small hand sprayer. After the spraying, the test plants were grown for an additional 3 weeks in the greenhouse, and the phytotoxicity was examined. The results are shown in Table 2. In the above foliar application, the test compounds were each formulated into an emulsifiable concentrate, and the required amount of the emulsifiable concentrate was dispersed in water for application at a spray volume of 5 liters per are and applied with the addition of a wetting agent. At the time of application, soybean was in a first trifoliate stage, cotton in an 1-leaf stage, sugarbeet in a 2-leaf stage, corn in a 2-leaf stage, wheat in a 2-leaf stage and rice plant in a 3-leaf stage.

TABLE 2

| Compound No. | Dosage (weight of active ingredient, g/are) | Phytotoxicity | | | | | |
|---|---|---|---|---|---|---|---|
| | | Soybean | Cotton | Sugargeet | Corn | Wheat | Rice plant |
| 3 | 20 | 0 | 1 | — | — | — | — |
| | 10 | 0 | 0 | — | — | — | — |
| 8 | 20 | 0 | 1 | — | — | — | 0 |
| | 10 | 0 | 0 | — | — | — | 0 |
| 9 | 10 | 1 | 1 | — | 0 | 0 | 0 |
| | 5 | 0 | 0 | — | 0 | 0 | 0 |
| 12 | 20 | — | — | — | 0 | 0 | — |
| | 10 | — | — | — | 0 | 0 | — |
| 13 | 20 | — | — | — | 1 | 0 | 1 |
| | 10 | — | — | — | 0 | 0 | 0 |
| 15 | 20 | 0 | — | — | — | 0 | — |
| | 10 | 0 | — | — | — | 0 | — |
| 21 | 20 | 1 | — | 1 | 0 | — | — |
| | 10 | 0 | — | 1 | 0 | — | — |
| 22 | 20 | 0 | 1 | — | 0 | 1 | — |
| | 10 | 0 | 1 | — | 0 | 0 | — |
| 23 | 20 | 0 | 1 | — | — | — | 0 |
| | 10 | 0 | 1 | — | — | — | 0 |
| 24 | 40 | 0 | — | — | — | — | — |
| | 20 | 0 | — | — | — | — | — |
| 31 | 10 | — | — | — | — | 1 | 1 |
| | 5 | — | — | — | — | 0 | 0 |
| 33 | 10 | 1 | — | — | 0 | 0 | — |
| 34 | 5 | 0 | — | — | 0 | 0 | — |
| | 20 | — | — | — | — | 0 | 0 |
| | 10 | — | — | — | — | 0 | 0 |
| 35 | 10 | — | — | — | — | 1 | — |
| | 5 | — | — | — | — | 0 | — |
| 36 | 20 | — | — | — | — | 0 | — |
| | 10 | — | — | — | — | 0 | — |
| 37 | 20 | 0 | — | — | 1 | — | 0 |
| | 10 | 0 | — | — | 0 | — | 0 |
| 38 | 40 | — | — | — | — | 0 | — |
| | 20 | — | — | — | — | 0 | — |
| 39 | 20 | 1 | — | — | 1 | 0 | — |
| | 10 | 0 | — | — | 0 | 0 | — |
| 48 | 20 | 0 | — | — | — | — | — |
| | 10 | 0 | — | — | — | — | — |
| 50 | 20 | — | — | — | — | 0 | — |
| | 10 | — | — | — | — | 0 | — |
| 51 | 20 | 1 | — | — | — | — | — |
| | 10 | 1 | — | — | — | — | — |
| 52 | 20 | 1 | — | — | — | — | — |
| | 10 | 0 | — | — | — | — | — |
| 59 | 20 | 1 | 1 | — | — | — | 0 |
| | 10 | 0 | 1 | — | — | — | 0 |
| 63 | 20 | 1 | — | — | — | 0 | — |
| | 10 | 0 | — | — | — | 0 | — |
| 64 | 20 | 1 | — | — | 0 | 0 | — |
| | 10 | 0 | — | — | 0 | 0 | — |
| 68 | 20 | — | — | — | 1 | — | 0 |
| | 10 | — | — | — | 0 | — | 0 |
| Chloroxuron | 10 | 2 | 5 | 5 | 4 | 3 | 2 |
| | 5 | 2 | 5 | 5 | 2 | 1 | 1 |
| Fluometuron | 20 | 4 | 2 | 5 | 3 | 4 | 4 |
| | 10 | 3 | 1 | 5 | 2 | 3 | 2 |

EXAMPLE 10

Pre-emergence application

Plastic trays (35 cm×25 cm×10 cm (high) were filled with upland field soil, and the seeds of redroot pigweed, common lambsquarters, radish, common purslane (*Portulaca oleracea*), large crabgrass, soybean, cotton, sugarbeet, corn, wheat and rice plants were separately sowed in the trays. The required amount of a wettable powder was dispersed in water and sprayed at a volume of 5 liters per are to the whole surface of the soil by means of a small hand sprayer. After the spraying, the trays were placed in a greenhouse for 20 days, and the phytotoxicity and herbicidal activity were examined. The results are shown in Table 3.

TABLE 3

| Compound No. | Dosage (weight of active ingredient, g/are) | Phytotoxicity | | | | | | Herbicidal activity | | | | |
|---|---|---|---|---|---|---|---|---|---|---|---|---|
| | | Soybean | Cotton | Sugarbeet | Corn | Wheat | Rice plant | Redroot pigweed | Common lambsquarters | Radish | Common purslane | Large crabgrass |
| 1 | 40 | 0 | 1 | — | 1 | — | 0 | 5 | 5 | 5 | 5 | 5 |
| | 20 | 0 | 1 | — | 0 | — | 0 | 5 | 5 | 5 | 5 | 4 |

TABLE 3-continued

| Compound No. | Dosage (weight of active ingredient, g/are) | Phytotoxicity | | | | | | Herbicidal activity | | | | |
|---|---|---|---|---|---|---|---|---|---|---|---|---|
| | | Soybean | Cotton | Sugar-beet | Corn | Wheat | Rice plant | Redroot pigweed | Common lambs-quarters | Radish | Common purslane | Large crabgrass |
| 2 | 40 | 0 | 0 | 1 | — | 0 | 0 | 5 | 5 | 5 | 5 | 4 |
| | 20 | 0 | 0 | 1 | — | 0 | 0 | 5 | 5 | 5 | 5 | 4 |
| 3 | 40 | 0 | 0 | — | — | — | 0 | 5 | 5 | 5 | 5 | 4 |
| | 20 | 0 | 0 | — | — | — | 0 | 5 | 5 | 5 | 5 | 3 |
| 8 | 40 | 0 | 0 | — | 0 | 0 | 0 | 5 | 5 | 5 | 5 | 5 |
| | 20 | 0 | 0 | — | 0 | 0 | 0 | 5 | 5 | 5 | 5 | 5 |
| 9 | 40 | 0 | 0 | 1 | 0 | 0 | 0 | 5 | 5 | 5 | 5 | 5 |
| | 20 | 0 | 0 | 0 | 0 | 0 | 0 | 5 | 5 | 5 | 5 | 5 |
| 13 | 40 | 1 | 0 | — | 0 | — | 0 | 5 | 5 | 5 | 5 | 4 |
| | 20 | 0 | 0 | — | 0 | — | 0 | 5 | 5 | 5 | 5 | 2 |
| 14 | 40 | 0 | — | — | — | 1 | 0 | 5 | 5 | 5 | 5 | 4 |
| | 20 | 0 | — | — | — | 0 | 0 | 5 | 5 | 5 | 5 | 3 |
| 16 | 40 | — | — | — | 0 | — | — | 5 | 5 | 5 | 5 | 5 |
| | 20 | — | — | — | 0 | — | — | 5 | 5 | 5 | 5 | 3 |
| 24 | 40 | 0 | 0 | — | — | — | 0 | 5 | 5 | 5 | 5 | 5 |
| | 20 | 0 | 0 | — | — | — | 0 | 5 | 5 | 5 | 5 | 3 |
| 26 | 40 | 1 | 1 | — | — | — | 1 | 5 | 5 | 5 | 5 | 4 |
| | 20 | 0 | 1 | — | — | — | 0 | 5 | 5 | 5 | 5 | 4 |
| 31 | 40 | — | 1 | — | — | 0 | 0 | 5 | 5 | 5 | 5 | 5 |
| | 20 | — | 0 | — | — | 0 | 0 | 5 | 5 | 5 | 5 | 4 |
| 34 | 40 | 0 | — | — | 1 | 0 | — | 5 | 5 | 5 | 5 | 3 |
| | 20 | 0 | — | — | 0 | 0 | — | 5 | 5 | 5 | 5 | 2 |
| 35 | 40 | 1 | — | — | — | 0 | 0 | 5 | 5 | 5 | 5 | 5 |
| | 20 | 0 | — | — | — | 0 | 0 | 5 | 5 | 5 | 5 | 4 |
| 46 | 40 | 0 | — | 1 | 1 | — | 0 | 5 | 5 | 5 | 5 | 4 |
| | 20 | 0 | — | 1 | 0 | — | 0 | 5 | 5 | 5 | 5 | 4 |
| 48 | 40 | 0 | 0 | — | 0 | 0 | — | 5 | 5 | 5 | 5 | 5 |
| | 20 | 0 | 0 | — | 0 | 0 | — | 5 | 5 | 5 | 5 | 4 |
| 51 | 40 | 1 | 0 | — | — | 1 | — | 5 | 5 | 5 | 5 | 5 |
| | 20 | 1 | 0 | — | — | 0 | — | 5 | 5 | 5 | 5 | 5 |
| 52 | 40 | — | 0 | — | — | — | 0 | 5 | 5 | 5 | 5 | 4 |
| | 20 | — | 0 | — | — | — | 0 | 5 | 5 | 5 | 5 | 4 |
| 53 | 40 | — | — | — | 0 | 0 | — | 5 | 5 | 5 | 5 | 4 |
| | 20 | — | — | — | 0 | 0 | — | 5 | 5 | 5 | 5 | 2 |
| 54 | 40 | — | 1 | — | — | — | — | 5 | 5 | 5 | 5 | 3 |
| | 20 | — | 0 | — | — | — | — | 5 | 5 | 5 | 5 | 2 |
| 55 | 40 | — | — | — | — | 1 | 0 | 5 | 5 | 5 | 5 | 4 |
| | 20 | — | — | — | — | 0 | 0 | 5 | 5 | 5 | 5 | 3 |
| 58 | 40 | 1 | 0 | — | 1 | — | — | 5 | 5 | 5 | 5 | 5 |
| | 20 | 0 | 0 | — | 0 | — | — | 5 | 5 | 5 | 5 | 3 |
| 59 | 40 | 1 | 0 | — | — | 1 | — | 5 | 5 | 5 | 5 | 4 |
| | 20 | 0 | 0 | — | — | 0 | — | 5 | 5 | 5 | 5 | 3 |
| 60 | 40 | — | — | — | 1 | 0 | — | 5 | 5 | 5 | 5 | 4 |
| | 20 | — | — | — | 0 | 0 | — | 5 | 5 | 5 | 5 | 3 |
| 61 | 40 | 1 | — | — | — | — | 0 | 5 | 5 | 5 | 5 | 3 |
| | 20 | 0 | — | — | — | — | 0 | 5 | 5 | 5 | 5 | 2 |
| 64 | 40 | — | 1 | — | — | 1 | — | 5 | 5 | 5 | 5 | 3 |
| | 20 | — | 0 | — | — | 0 | — | 5 | 5 | 4 | 5 | 2 |
| 67 | 40 | 1 | — | — | 0 | — | 0 | 5 | 5 | 5 | 5 | 5 |
| | 20 | 0 | — | — | 0 | — | 0 | 5 | 5 | 5 | 5 | 4 |
| 68 | 40 | 1 | 1 | — | — | — | — | 5 | 5 | 5 | 5 | 5 |
| | 20 | 0 | 0 | — | — | — | — | 5 | 5 | 5 | 5 | 4 |
| Chloramben | 20 | 0 | 4 | — | 4 | 2 | 2 | 4 | 5 | 3 | 5 | 5 |
| | 10 | 0 | 4 | — | 3 | 1 | 1 | 4 | 3 | 1 | 5 | 4 |
| Chloroxuron | 40 | 0 | — | 4 | — | — | 1 | 4 | 4 | 3 | 4 | 1 |
| | 20 | 0 | — | 3 | — | — | 0 | 4 | 3 | 2 | 3 | 0 |

EXAMPLE 11

Paddy rice test

Wagner's pots (1/5000 are) were each filled with 1.5 kg of paddy field soil containing the seeds of weeds and kept under flooded conditions. The seedlings of rice plants at a 3-leaf stage were transplanted thereto, and after the seeds of barnyard grass were sown therein, the seedlings were grown for 5 days in a greenhouse. Thereafter, the required amount of the wettable powder of each test compound was diluted with water and applied to the soil under flooded conditions. Twenty days after the application, the evaluation of herbicidal activity and phytotoxicity was made on the rice plants and barnyard grass as well as broad-leaved weeds (e.g. pickerel weed (*Monochoria vagianalis*), false pimpernel (*Linderna pyxidaria*), toothcup (*Rotala indica*)) and nutsedge sp. (*Cyperus difformis*). The results are shown in Table 4.

TABLE 4

| Compound No. | Dosage (weight of active ingredient, g/are) | Phytotoxicity Rice plant | Herbicidal activity | | |
|---|---|---|---|---|---|
| | | | Barnyard grass | Broad-leaved weeds | False pimpernel |
| 4 | 20 | 0 | 4 | 5 | 5 |
| | 10 | 0 | 3 | 5 | 5 |
| 5 | 20 | 0 | 4 | 5 | 5 |
| | 10 | 0 | 4 | 5 | 5 |
| 6 | 20 | 0 | 4 | 5 | 5 |

TABLE 4-continued

| Compound No. | Dosage (weight of active ingredient, g/are) | Phytotoxicity Rice plant | Herbicidal activity Barnyard grass | Herbicidal activity Broad-leaved weeds | Herbicidal activity False pimpernel |
|---|---|---|---|---|---|
| 7 | 10 | 0 | 3 | 5 | 5 |
|  | 20 | 0 | 4 | 5 | 5 |
| 8 | 10 | 0 | 3 | 5 | 5 |
|  | 20 | 0 | 5 | 5 | 5 |
| 9 | 10 | 0 | 4 | 5 | 5 |
|  | 20 | 0 | 5 | 5 | 5 |
| 11 | 10 | 0 | 4 | 5 | 5 |
|  | 20 | 0 | 4 | 5 | 5 |
| 12 | 10 | 0 | 3 | 5 | 5 |
|  | 20 | 0 | 4 | 5 | 5 |
| 13 | 10 | 0 | 4 | 5 | 5 |
|  | 20 | 0 | 5 | 5 | 5 |
| 15 | 10 | 0 | 3 | 5 | 5 |
|  | 20 | 0 | 4 | 5 | 5 |
| 17 | 10 | 0 | 4 | 5 | 5 |
|  | 20 | 0 | 4 | 5 | 5 |
| 18 | 20 | 0 | 3 | 5 | 5 |
|  | 40 | 0 | 4 | 5 | 5 |
| 20 | 10 | 0 | 4 | 5 | 5 |
|  | 20 | 0 | 4 | 5 | 5 |
| 22 | 10 | 0 | 4 | 5 | 5 |
|  | 20 | 0 | 4 | 5 | 5 |
| 23 | 10 | 0 | 3 | 5 | 5 |
|  | 20 | 0 | 4 | 5 | 5 |
| 25 | 20 | 0 | 3 | 5 | 5 |
|  | 40 | 0 | 4 | 5 | 5 |
| 27 | 10 | 0 | 3 | 5 | 5 |
|  | 20 | 0 | 4 | 5 | 5 |
| 28 | 20 | 0 | 3 | 5 | 5 |
|  | 40 | 0 | 3 | 5 | 5 |
| 29 | 10 | 0 | 3 | 5 | 5 |
|  | 20 | 0 | 4 | 5 | 5 |
| 30 | 20 | 0 | 3 | 5 | 5 |
|  | 40 | 0 | 4 | 5 | 5 |
| 31 | 10 | 0 | 4 | 5 | 5 |
|  | 20 | 0 | 5 | 5 | 5 |
| 32 | 10 | 0 | 3 | 5 | 5 |
|  | 20 | 0 | 4 | 5 | 5 |
| 33 | 10 | 0 | 3 | 5 | 5 |
|  | 20 | 0 | 5 | 5 | 5 |
| 34 | 10 | 0 | 3 | 5 | 5 |
|  | 20 | 0 | 4 | 5 | 5 |
| 35 | 10 | 0 | 4 | 5 | 5 |
|  | 20 | 0 | 5 | 5 | 5 |
| 36 | 10 | 0 | 3 | 5 | 5 |
|  | 20 | 0 | 4 | 5 | 5 |
| 37 | 10 | 0 | 2 | 5 | 5 |
|  | 20 | 0 | 3 | 5 | 5 |
| 38 | 20 | 0 | 3 | 5 | 5 |
|  | 40 | 0 | 4 | 5 | 5 |
| 39 | 10 | 0 | 4 | 5 | 5 |
|  | 20 | 0 | 4 | 5 | 5 |
| 40 | 10 | 0 | 3 | 5 | 5 |
|  | 20 | 0 | 3 | 5 | 5 |
| 41 | 20 | 0 | 3 | 5 | 5 |
|  | 40 | 0 | 4 | 5 | 5 |
| 46 | 10 | 0 | 4 | 5 | 5 |
|  | 20 | 0 | 4 | 5 | 5 |
| 47 | 20 | 0 | 3 | 5 | 5 |
|  | 40 | 0 | 4 | 5 | 5 |
| 48 | 10 | 0 | 5 | 5 | 5 |
|  | 20 | 0 | 5 | 5 | 5 |
| 50 | 10 | 0 | 2 | 5 | 5 |
|  | 20 | 0 | 4 | 5 | 5 |
| 51 | 10 | 0 | 3 | 5 | 5 |
|  | 20 | 0 | 5 | 5 | 5 |
| 52 | 10 | 0 | 2 | 5 | 5 |
|  | 20 | 0 | 4 | 5 | 5 |
| 55 | 10 | 0 | 3 | 5 | 5 |
|  | 20 | 0 | 4 | 5 | 5 |
| 57 | 20 | 0 | 3 | 5 | 4 |
|  | 40 | 0 | 4 | 5 | 5 |
| 58 | 10 | 0 | 3 | 5 | 5 |
|  | 20 | 0 | 4 | 5 | 5 |
| 60 | 20 | 0 | 3 | 5 | 5 |
|  | 40 | 0 | 4 | 5 | 5 |
| 61 | 10 | 0 | 2 | 5 | 5 |
|  | 20 | 0 | 4 | 5 | 5 |
| 62 | 10 | 0 | 3 | 5 | 5 |
|  | 20 | 0 | 3 | 5 | 5 |
| 64 | 10 | 0 | 5 | 5 | 5 |
|  | 20 | 1 | 5 | 5 | 5 |
| 65 | 20 | 0 | 2 | 4 | 5 |
|  | 40 | 0 | 3 | 5 | 5 |
| 67 | 10 | 0 | 3 | 5 | 5 |
|  | 20 | 1 | 5 | 5 | 5 |
| 68 | 10 | 0 | 3 | 5 | 5 |
|  | 20 | 0 | 4 | 5 | 5 |
| MCPA | 5 | 2 | 2 | 5 | 5 |
|  | 10 | 2 | 3 | 5 | 5 |
|  | 20 | 3 | 4 | 5 | 5 |

EXAMPLE 12

(A) Soil treatment before emergence

Plastic trays (35 cm×25 cm×10 cm (high)) were filled with upland field soil, and the seeds of wheat, blackgrass, annual bluegrass, black nightshade, common lambsquarters, shepherdspurse, bedstraw, chickweed, birdseye speedwell, red deadnettle and redroot pigweed were separately sown in the trays. The required amount of an emulsifiable concentrate was dispersed in water and sprayed at a volume of 10 liters per are to the surface of the soil by means of a small hand sprayer and the surface layer soil to the depth of 4 cm was well mixed. After the spraying, the trays were placed in a greenhouse for 3 weeks, and the phytotoxicity and herbicidal activity were examined. The results are shown in Table 5.

(B) Foliage treatment after emergence

Plastic trays (35 cm×25 cm×10 cm (high)) were filled with upland field soil, and the seeds of wheat, blackgrass, annual bluegrass, black nightshade, common lambsquarters, shepherdspurse, bedstraw, chickweed, birdseye speedwell, red deadnettle and redroot pigweed were separately sown in the trays. The required amount of an emulsifiable concentrate was dispersed in water and applied with the addition of a wetting agent at a volume of 5 liters per are to the test plants by means of a small hand sprayer. After the spraying, the trays were placed in a greenhouse for 3 weeks, and the phytotoxicity and herbicidal activity were examined. The results are also shown in Table 5.

TABLE 5

| Compound No. | Treatment method | Dosage (weight of active ingredient, g/are) | Phytotoxicity Wheat | Herbicidal activity |  |  |  |  |  |  |  |  |  |
|---|---|---|---|---|---|---|---|---|---|---|---|---|---|
| | | | | Black-grass | Annual blue-grass | Black nightshade | Common lambsquarters | Shepherdspurse | Bed-straw | Chick-weed | Birdseye speedwell | Red deadnettle | Redroot pigweed |
| 8 | A | 80 | 0 | 5 | 5 | 5 | 5 | 5 | 5 | 5 | 5 | 5 | 5 |
| | | 40 | 0 | 4 | 5 | 5 | 5 | 5 | 5 | 5 | 5 | 5 | 5 |
| | | 20 | 0 | 2 | 4 | 5 | 5 | 5 | 4 | 5 | 5 | 5 | 5 |
| | | 10 | 0 | 2 | 4 | 5 | 5 | 5 | 4 | 5 | 5 | 4 | 5 |
| 51 | A | 80 | 0 | 5 | 5 | 5 | 5 | 5 | 5 | 5 | 5 | 5 | 5 |
| | | 40 | 0 | 4 | 5 | 5 | 5 | 5 | 5 | 5 | 5 | 5 | 5 |
| | | 20 | 0 | 4 | 4 | 5 | 5 | 5 | 5 | 5 | 5 | 5 | 5 |
| | | 10 | 0 | 3 | 3 | 5 | 5 | 5 | 4 | 5 | 5 | 5 | 5 |
| Control (e) | A | 80 | 0 | 4 | 5 | 5 | 5 | 5 | 5 | 5 | 5 | 5 | 5 |
| | | 40 | 0 | 4 | 3 | 5 | 5 | 5 | 5 | 5 | 5 | 5 | 5 |
| | | 20 | 0 | 2 | 1 | 5 | 5 | 5 | 4 | 5 | 5 | 4 | 5 |
| | | 10 | 0 | 1 | 1 | 5 | 5 | 5 | 2 | 5 | 5 | 3 | 4 |
| 9 | A | 80 | 1 | 5 | 5 | 5 | 5 | 5 | 5 | 5 | 5 | 5 | 5 |
| | | 40 | 0 | 5 | 5 | 5 | 5 | 5 | 5 | 5 | 5 | 5 | 5 |
| | | 20 | 0 | 4 | 5 | 5 | 5 | 5 | 4 | 5 | 5 | 5 | 5 |
| | | 10 | 0 | 2 | 4 | 5 | 5 | 5 | 3 | 5 | 5 | 5 | 5 |
| Control (a) | A | 80 | 1 | 4 | 5 | 5 | 5 | 5 | 5 | 5 | 5 | 5 | 5 |
| | | 40 | 0 | 4 | 4 | 5 | 5 | 5 | 4 | 5 | 5 | 5 | 5 |
| | | 20 | 0 | 2 | 3 | 4 | 5 | 5 | 2 | 4 | 5 | 5 | 4 |
| 13 | A | 80 | 0 | 4 | 4 | 5 | 5 | 5 | 5 | 5 | 5 | 5 | 5 |
| | | 40 | 0 | 3 | 2 | 5 | 5 | 5 | 5 | 5 | 5 | 5 | 5 |
| | | 20 | 0 | 3 | 2 | 4 | 5 | 5 | 4 | 5 | 5 | 5 | 4 |
| | | 10 | 0 | 2 | 1 | 3 | 4 | 5 | 3 | 5 | 3 | 4 | 4 |
| Control (b) | A | 80 | 2 | 4 | 3 | 4 | 4 | 5 | 4 | 5 | 4 | 5 | 4 |
| | | 40 | 1 | 2 | 2 | 3 | 4 | 5 | 3 | 4 | 3 | 5 | 4 |
| | | 20 | 0 | 2 | 1 | 2 | 3 | 4 | 1 | 3 | 3 | 4 | 4 |
| 13 | B | 40 | 1 | 5 | 5 | 5 | 5 | 5 | 5 | 5 | 5 | 5 | 5 |
| | | 20 | 0 | 5 | 5 | 5 | 5 | 5 | 5 | 5 | 5 | 5 | 5 |
| | | 10 | 0 | 4 | 4 | 5 | 5 | 5 | 5 | 5 | 5 | 5 | 5 |
| | | 5 | 0 | 4 | 3 | 5 | 5 | 5 | 5 | 5 | 5 | 4 | 5 |
| Control (b) | B | 40 | 3 | 5 | 4 | 5 | 5 | 5 | 5 | 5 | 5 | 5 | 5 |
| | | 20 | 1 | 4 | 4 | 5 | 5 | 5 | 5 | 5 | 5 | 5 | 5 |
| | | 10 | 1 | 3 | 2 | 5 | 5 | 5 | 4 | 5 | 5 | 4 | 5 |
| | | 5 | 0 | 1 | 2 | 4 | 5 | 5 | 3 | 5 | 4 | 3 | 4 |
| 34 | A | 80 | 0 | 4 | 5 | 5 | 5 | 5 | 5 | 5 | 5 | 5 | 5 |
| | | 40 | 0 | 4 | 3 | 5 | 5 | 5 | 5 | 5 | 5 | 5 | 5 |
| | | 20 | 0 | 3 | 2 | 5 | 5 | 5 | 5 | 5 | 5 | 5 | 5 |
| | | 10 | 0 | 1 | 2 | 5 | 5 | 5 | 4 | 5 | 5 | 5 | 4 |
| Control (c) | A | 80 | 0 | 2 | 3 | 5 | 5 | 5 | 4 | 5 | 5 | 5 | 5 |
| | | 40 | 0 | 2 | 3 | 4 | 5 | 5 | 3 | 5 | 4 | 4 | 5 |
| | | 20 | 0 | 1 | 1 | 3 | 5 | 4 | 2 | 5 | 2 | 4 | 5 |
| | | 10 | 0 | 1 | 0 | 1 | 3 | 2 | 2 | 3 | 1 | 1 | 3 |
| 34 | B | 20 | 0 | 5 | 5 | 5 | 5 | 5 | 5 | 5 | 5 | 5 | 5 |
| | | 10 | 0 | 5 | 5 | 5 | 5 | 5 | 5 | 5 | 5 | 5 | 5 |
| | | 5 | 0 | 5 | 5 | 5 | 5 | 5 | 5 | 5 | 5 | 5 | 5 |
| | | 2.5 | 0 | 4 | 5 | 5 | 5 | 5 | 4 | 5 | 5 | 5 | 5 |
| Control (c) | B | 20 | 2 | 5 | 5 | 5 | 5 | 5 | 5 | 5 | 5 | 5 | 5 |
| | | 10 | 2 | 5 | 5 | 5 | 5 | 5 | 5 | 5 | 5 | 5 | 5 |
| | | 5 | 1 | 4 | 4 | 5 | 5 | 5 | 4 | 5 | 4 | 5 | 5 |
| | | 2.5 | 0 | 4 | 2 | 5 | 5 | 5 | 3 | 5 | 3 | 5 | 5 |
| 38 | A | 80 | 0 | 4 | 3 | 5 | 5 | 5 | 5 | 5 | 5 | 5 | 5 |
| | | 40 | 0 | 2 | 3 | 5 | 5 | 5 | 5 | 5 | 5 | 5 | 5 |
| | | 20 | 0 | 1 | 2 | 5 | 5 | 5 | 4 | 5 | 5 | 5 | 5 |
| | | 10 | 0 | 0 | 0 | 4 | 5 | 5 | 3 | 4 | 3 | 4 | 5 |
| Control (d) | A | 80 | 0 | 0 | 0 | 4 | 5 | 5 | 4 | 5 | 5 | 4 | 4 |
| | | 40 | 0 | 0 | 0 | 2 | 5 | 4 | 3 | 4 | 4 | 4 | 3 |
| | | 20 | 0 | 0 | 0 | 0 | 3 | 3 | 1 | 2 | 3 | 3 | 2 |

What is claimed is:

1. A compound of the formula:

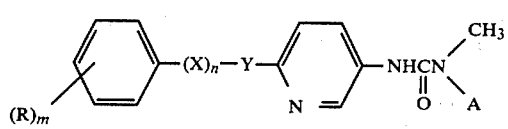

wherein A is a hydrogen atom, a methyl group or a methoxy group, X is a straight or branched $C_1$–$C_4$ alkylene chain, Y is an oxygen atom or a sulfur atom, R, which may be the same or different, is a lower alkyl group, a lower alkoxy group, a trifluoromethyl group, a chlorine atom, a bromine atom or a fluorine atom, m is an integer of 0 to 5 and n is an integer of 0 or 1, provided that in case of R being a fluorine atom, m is an integer of 0 to 5 and in case of R being other than a fluorine atom, m is an integer of 0 to 3.

2. A compound of the formula:

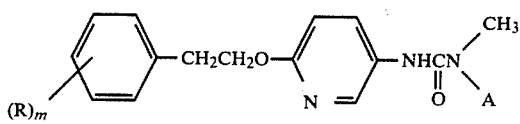

wherein A is a methyl group or a methoxy group, R is a lower alkyl group, a lower alkoxy group, a chlorine atom, a bromine atom or a fluorine atom and m is an integer of 0 or 1.

3. A compound of the formula:

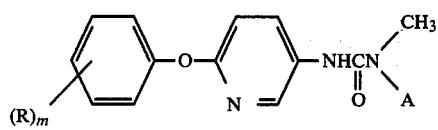

wherein A is a methyl group or a methoxy group, R is a trifluoromethyl group, a chlorine atom, a bromine atom or a fluorine atom and m is an integer of 1 to 5 when R is a fluorine atom, an integer of 1 to 2 when R is a chlorine atom or a bromine atom or an integer of 1 when R is a trifluoromethyl group.

4. The compound according to claim 1, which is N'-[2-(4-methylphenethyloxy)pyridyl-5-]-N-methoxy-N-methylurea.

5. The compound according to claim 1, which is N'-[2-(phenethyloxy)pyridyl-5]-N-methoxy-N-methylurea.

6. The compound according to claim 1, which is N'-[2-(4-fluorophenethyloxy)pyridyl-5-]-N,N-dimethylurea.

7. The compound according to claim 1, which is N'-[2-(4-isopropoxyphenethyloxy)pyridyl-5]-N-methoxy-N-methylurea.

8. The compound according to claim 1, which is N'-[2-(3-trifluoromethylphenoxy)pyridyl-5]-N-methoxy-N-methylurea.

9. The compound according to claim 1, which is N'-[2-(3-trifluoromethylphenoxy)pyridyl-5]-N,N-dimethylurea.

10. The compound according to claim 1, which is N'-[2-(pentafluorophenoxy)pyridyl-5]-N,N-dimethylurea.

11. A herbicidal composition comprising as an active ingredient at least one of the compounds claimed in claim 1.

12. The composition according to claim 1, wherein the concentration of the active ingredient is from about 1 to 80% by weight.

13. A method for controlling weeds which comprises applying the compound according to claim 1 to the area where the weeds grow.

14. A method of selectively combating weeds in the cultivation of sugarbeet, soybean, cotton, rice, wheat or corn, which comprises applying a herbicidally effective amount of the compound according to claim 1 to the area where the sugarbeet, soybean, cotton, rice, wheat or corn crop is cultivated.

* * * * *